US008809494B2

(12) United States Patent
Bergman et al.

(10) Patent No.: US 8,809,494 B2
(45) Date of Patent: Aug. 19, 2014

(54) METHOD AND COMPOSITIONS FOR PREVENTION AND TREATMENT OF MALARIA INFECTIONS

(75) Inventors: Lawrence W. Bergman, Lansdale, PA (US); Akhil B. Vaidya, Wynnewood, PA (US)

(73) Assignee: Drexel University, Philadelphia, PA (US)

( * ) Notice: Subject to any disclaimer, the term of this patent is extended or adjusted under 35 U.S.C. 154(b) by 938 days.

(21) Appl. No.: 11/718,772

(22) PCT Filed: Nov. 17, 2005

(86) PCT No.: PCT/US2005/041509
§ 371 (c)(1),
(2), (4) Date: Jul. 20, 2007

(87) PCT Pub. No.: WO2006/055623
PCT Pub. Date: May 26, 2006

(65) Prior Publication Data
US 2008/0274113 A1    Nov. 6, 2008

Related U.S. Application Data

(60) Provisional application No. 60/628,572, filed on Nov. 17, 2004.

(51) Int. Cl.
*A61K 38/00* (2006.01)
*C07K 1/00* (2006.01)
*A61K 39/015* (2006.01)
*A61K 39/00* (2006.01)

(52) U.S. Cl.
USPC ........... 530/300; 530/324; 530/806; 530/820; 514/1.1; 424/272.1; 424/191.1

(58) Field of Classification Search
None
See application file for complete search history.

(56) References Cited

U.S. PATENT DOCUMENTS 6,090,611 A      7/2000  Covacci et al.
2007/0048301 A1*  3/2007  Bodary-Winter et al. ........ 435/6

OTHER PUBLICATIONS

UniProt accession No. Q8IJB7 PLAF7, Mar. 1, 2003.*
Ellis RW. Vaccines, (Eds) Plotkin et al., W.B. Saunders Company, Philadelphia, Chapter 29, 568-575, 1988.*
Cruse et al. Illustrated Dictionary of Immunology, 2nd Edn., CRC Press, pp. 46, 166 and 382, 2003.*
Harlow et al. et al. In: Antibodies: A laboratory Manual. Cold Spring Harbor Laboratory, Chapter 5, p. 76, 1988.*
Campbell AM. In: Monoclonal Antibody Technology. Elsevier Science Publishers, The Netherlands, Chapter 1, pp. 1-32, 1984.*
Andrysiak et al. Infect. Immun. 54: 609-612, 1986.*
The Webster's II New Riverside University Dictionary, p. 933, 1984.*
Illustrated Stedman's Medical Dictionary, 24th Edition, p. 707, 1982.*
Aikawa et al., "Erythrocyte Entry by Malarial Parasites", J. Cell Biology 1978 77:72-82.
Baldi et al., "RAP1 controls rhoptry targeting of RAP2 in the malaria parasite *Plasmodium falciparum*", The EMBO Journal 2000 19(11):2435-2443.
Bergman et al., "A merozoite protein that interacts with the actin-myosin motor via aldolase", MAM 2004 Poster Abstracts/Experimental Parasitology 2003 105:30.
Bergman et al., "Myosin A tail domain interacting protein (MTIP) localizes to the inner membrane complex of *Plasmodium* sporozoites", Journal of Cell Science 2003 116:39-49.
Crabb et al., "Targeted Gene Disruption Shows That Knobs Enable Malaria-Infected Red Cells to Cytoadhere under Physiological Shear Stress", Cell 1997 89:287-296.
Deans et al., "Biosynthesis of a Putative Protective *Plasmodium knowlesi* Merozoite Antigen", Molecular and Biochemical Parasitology 1984 11:189-204.
Dessens et al., "CTRP is essential for mosquito infection by malaria ookinetes", The EMBO Journal 1999 18 (22):6221-6227.
Dobrowolski et al., "Participation of myosin in gliding motility and host cell invasion by *Toxoplasma gondii*", Molecular Microbiology 1997 26(1):163-173.
Fields et al., "A novel genetic system to detect protein-protein interactions", Nature 1989 340:245-246.
Holder et al., "Primary structure of the precursor to the three major surface antigens of *Plasmodium falciparum* merozoites", Nature 1985 317:270-273.
Holder et al., "The Three Major Antigens on the Surface of *Plasmodium falciparum* Merozoites are Derived from a Single High Molecular Weight Precursor", J. Exp. Med. 1984 160:624-629.
Hodder et al., "Specificity of the Protective Antibody Response to Apical Membrane Antigen 1", Infection and Immunity 2001 69(5):3286-3294.
Klotz et al., "A 60-kDa *Plasmodium falciparum* protein at the moving junction formed between merozoite and erythrocyte during invasion", Molecular and Biochemical Parasitology 1989 36:177-186.
Luban et al., "The yeast two-hybrid system for studying protein-protein interactions", Current Opinion in Biotechnology 1995 6:59-64.
Marshall et al., "A Second Merozoite Surface Protein (MSP-4) of *Plasmodium falciparum* That Contains an Epidermal Growth Factor-Like Domain", Infection and Immunity 1997 65(11):4460-4467.
Marshall et al., "Close linkage of three merozoite surface protein genes on chromosome 2 of *Plasmodium falciparum*", Molecular and Biochemical Parasitology 1998 94:13-25.

(Continued)

Primary Examiner — S. Devi
(74) Attorney, Agent, or Firm — Saul Ewing LLP; Kathryn Doyle

(57) ABSTRACT

Isolated proteins and nucleic acid sequence encoding such protein that interacts with a red blood cell to be invaded by a malaria parasite and link with a component of the actin-myosin based machinery of the malaria parasite are provided. In addition methods for identifying agents which inhibit the function of these proteins as chemotherapeutic and/or immunologic agents for treatment and prevention of malaria infections are provided. Compositions for treatment and prevention of malaria infections and methods for preventing and treating malaria infections are also provided.

1 Claim, No Drawings

(56) References Cited

OTHER PUBLICATIONS

Menard, Robert, "Gliding motility and cell invasion by Apicomplexa:insights from the *Plasmodium* sporozoite", Cellular Microbiology 2001 3(2):63-73.

Perrin et al., "Immunization with *Plasmodium falciparum* Merozoite Surface Antigen Induces a Partial Immunity in Monkeys", J. Clin. Invest. 1985 75:1718-1721.

Michel et al., "Formation of a Close Junction During Invasion of Erythrocytes by *Toxoplasma gondii* in Vitro", International Journal for Parasitology 1980 10:309-313.

Miller et al., "Interaction Between Cytochalasin B-Treated Malarial Parasites and Erythrocytes", The Journal of Experimental Medicine 1979 149:172-184.

Morrissette et al., "Cytoskeleton of Apicomplexan Parasites", Microbiology and Molecular Biology Reviews 2002 66 (1):21-38.

Mota et al., "Invasion of mammalian host cells by *Plasmodium sporozoites*", BioEssays 2002 24:149-156.

Narum et al., "Differential localization of full-length and processed forms of PF83/AMA-1 an apical membrane antigen of *Plasmodium falciparum* merozoites", Molecular and Biochemical Parasitology 1994 67:59-68.

Perkins et al., "Sialic Acid-Dependent Binding of *Plasmodium falciparum* Merozoite Surface Antigen, Pf200, to Human Erythrocytes", The Journal of Immunology 1988 141(9):3190-3196.

Peterson et al., "Integral Membrane Protein Located in the Apical Complex of *Plasmodium falciparum*", Molecular and Cellular Biology 1989 9(7):3151-3154.

Pinder et al., "Actomyosin motor in the merozoite of the malaria parasite, *Plasmodium falciparum*:implications for red cell invasion", Journal of Cell Science 1998 111:1831-1839.

Reed et al., "Targeted disruption of an erythrocyte binding antigen in *Plasmodium falciparum* is associated with a switch toward a sialic acid-independent pathway of invasion", Proc. Natl. Acad. Sci. USA 2000 97(13):7509-7514.

Ridley et al., "Characterization and sequence of a protective rhoptry antigen from *Plasmodium falciparum*", Molecular and Biochemical Parasitology 1990 41:125-134.

Sim et al., "*Plasmodium falciparum*:Further Characterization of a Functionally Active Region of the Merozoite Invasion Ligand EBA-175", Experimental Parasitology 1994 78:259-268.

Sinnis et al., "Structural and Functional Properties of Region II-Plus of the Malaria Circumsporozoite Protein", J. Exp. Med. 1994 180:297-306.

Smythe et al., "Identification of two integral membrane proteins of *Plasmodium falciparum*", Proc. Natl. Acad. Sci. USA 1988 85:5195-5199.

Stewart et al., "Malaria Sporozoites Leave Behind Trails of Circumsporozoite Protein During Gliding Motility", J. Protozool 1988 35(3):389-393.

Stewart et al., "*Plasmodium berghei* Sporozoite Invasion Is Blocked In Vitro by Sporozoite-Immobilizing Antibodies", Infection and Immunity 1986 51(3):859-864.

Sultan et al., "Complementation of *Plasmodium berghei* TRAP knockout parasites using human dihydrofolate reductase gene as a selectable marker", Molecular & Biochemical Parasitology 2001 113:151-156.

Templeton et al., "Developmental arrest of the human malaria parasite *Plasmodium falciparum* within the mosquito midgut via CTRP gene disruption", Molecular Microbiology 2000 36(1):1-9.

Wesseling et al., "Nucleotide sequence and deduced amino acid sequence of a *Plasmodium falciparum* actin gene", Molecular and Biochemical Parasitology 1988 27:313-320.

Wesseling et al., "Stage-specific expression and genomic organization of the actin genes of the malaria parasite *Plasmodium falciparum*", Molecular and Biochemical Parasitology 1989 35:167-176.

Wu et al., "Transformation of *Plasmodicum falciparum* malaria parasites by homologous integration of plasmids that confer resistance to pyrimethamine", Proc. Natl. Acad. Sci. USA 1996 93:1130-1134.

Yuda et al., "Targeted Disruption of the *Plasmodium berghei* CTRP Gene Reveals Its Essential Role in Malaria Infection of the Vector Mosquito", J. Exp. Med. 1999 190(11):1711-1715.

Gardner, et al., "Genome sequence of the human malaria parasite *Plasmodium falciparum*" (2002) Nature vol. 419:498-511 and Supplemental Figure J.

* cited by examiner

METHOD AND COMPOSITIONS FOR PREVENTION AND TREATMENT OF MALARIA INFECTIONS

This patent application claims the benefit of priority from U.S. Provisional Application Ser. No. 60/628,572 filed Nov. 17, 2004, teachings of which are herein incorporated by reference in their entirety.

FIELD OF THE INVENTION

A protein, referred to herein as PfMTI-1, and orthologs thereof have now been identified as providing a key molecular link for malaria parasites between the red blood cell, which is to be invaded, and the actin myosin based motor machinery of the parasite that drives the invasion process. Inhibition of the function of this protein or a homolog or ortholog thereof or a nucleic acid encoding this protein or a homolog or ortholog thereof prevents the parasite from invading red blood cells and is expected to prevent or lessen the clinical severity of malaria infection. Accordingly, the present invention provides methods for development of compositions for use in immunologic and chemotherapeutic therapies for treatment and prevention of malaria. Compositions and methods for use of these compositions in the treatment and prevention of malaria are also provided.

BACKGROUND OF THE INVENTION

Presently, malaria is a significant burden on humans. The parasite responsible for this disease continues to develop resistance to antimalarial drugs and there is no suitable vaccine to control the disease. These two major features ensure that malaria remains a major global health problem. *Plasmodium falciparum* causes the most severe form of the disease in humans and is responsible for 200-300 million infections per year. Greater than two million people die as a result of the disease annually. The development of an effective vaccine and the development of new and inexpensive antimalarial drugs remain top priorities in the world health community.

A key process to target for both vaccine and drug development research is the process of parasite invasion. Of the various forms of the parasite, three stages must have the ability to invade host cells: the ookinete, the sporozoite and the merozoite. There are both common features as well as unique features during the invasion process by each form. For example, although the invasive stages of the parasite are morphologically and biochemically different from one another, they share a highly conserved structural organization and special organelles called micronemes and rhopteries (for review see Sinnis and Sini, Trends in Microb. 1997 5:52-58; Pinder et al, J. Cell Sci. 2000 111:1831-1839; Chitnis, C. E. Curr. Op. in Hemat. 2001 8:85-91; and Mota and Rodriquez, Bioessays 2002 24:149-156). While function of these conserved structures has not been fully clarified, it is known that they are required for host cell invasion. All of these common structures confer some similarity to target cell invasion; the specific details in each case, however, differ. Each invasive stage of the parasite has a different target cell specificity, which is believed to be governed by a specific receptor-ligand type interaction. Furthermore, the invasion of the host cell appears to be an active process, which requires an actin-myosin based motility system to enter the host cell (Pinder et al, J. Cell Sci. 2000 111:1831-1839 and Morrissette and Sibley Microb. Mol. Bio. Rev. 2002 66:21-38).

In the case of hepatocyte invasion by sporozoites, injection of a very small number of *Plasmodium* sporozoites is sufficient to initiate infection, suggesting that the invasion process is extremely efficient. Furthermore, the process of hepatocyte invasion is extremely rapid, occurring within minutes after the infectious bite of the mosquito. The efficiency and rapidity of sporozoite invasion suggests that it involves specific interactions between parasite-encoded surface proteins and host molecules. Several lines of evidence suggest that the circumsporozoite protein (CS) plays a key role in this process (Stewart et al. Infect. Immunol. 1986 51:859-864; Stewart and Vanderberg J. Protozol. 1988 35:389-393; Menard, R. Cell Microb. 2001 3:63-73; Mota and Rodriquez Bioessays 2002 24:149-156). The CS protein of all *Plasmodium* species contains a highly conserved region, called region H, that is also found in the type I repeats of thrombospondin and some other adhesion molecules. It is believed that region H of CS binds to glycosaminoglycan chains of heparin sulfate proteoglycans (HSPGS) that are found on the surface of hepatocytes (Sinnis et al. J. Exp. Med. 1994 180:297-306). This binding is required for sporozoite attachment to hepatocytes, but is not necessary for invasion. Subsequent invasion with formation of a parasitophoros vacuole is tightly associated with exocytosis of the apical organelles. The attachment of the parasite to the host cell also triggers a transient cytosolic $Ca^{2+}$ increase that is required for invasion. This increase in the $Ca^{2+}$ concentration seems to induce the exocytosis of micronemes, a process required for the formation of the moving junction and the internalization of the parasite. Whether this increase in $Ca^{2+}$ concentration is also required for activation of the actin-myosin based motility system, as seen with other non-Apicomplexan motility systems, is not known. The exocytosis of the apical organelles results in the release of the TRAP (Thrombospondin-related anonymous protein) molecule and its distribution along the surface of the sporozoite. TRAP is a transmembrane protein that contains two well-characterized adhesive modules, an A domain of Von Willebrand factor and a type 1 repeat of thrombospondin, in its extracellular domain. TRAP (−) parasites, created by gene-targeting technology in *Plasmodium*, are unable to invade mosquito salivary glands or infect liver cells in vivo after intravenous injection, suggesting that TRAP plays a key role in the invasion process (Sultan et al. Mol. Biochem. Parasitol. 1997 113:151-156). A structurally related molecule, *Plasmodium* CTRP, produced by the ookinete stage, probably plays a similar role as inactivation of CTRP in *Plasmodium berghei* and *Plasmodium falciparum* showed that CTRP is necessary for ookinete transformation into an oocyst, a stage of the life cycle that requires ookinete migration through the midget epithelium of the mosquito (Dessens et al. EMBO J. 1999 18:6221-6227; Yuda et al. J. Exp. Med. 1999 190:1711-1715; Templeton et al. Mol. Microb. 2000 36:1-9).

The merozoite form of the asexual life cycle in the blood stage attaches to the surface of the red blood cell (RBC) which initiates the invasion process of this host cell. Many of the surface proteins of the merozoite are thus exposed to the immune system and consequently are potential vaccine candidates. Many of these proteins are thought to play a role in merozoite invasion of RBCs but the details of their function and interactions remain unclear at best. Merozoite invasion takes place following initial interaction with the RBC surface followed by re-orientation to allow the apical end of the parasite to interact with the membrane of the host cell. This re-orientation allows the contents of the apical organelles to be released and a tight junction is formed between the merozoite surface and the RBC membrane. The tight junction moves along the surface of the merozoite, possibly via force generated by the actin-myosin motor, until the membrane fuses at the posterior end of the parasite, resulting in the formation of the parasitophorous vacuole contain the newly invaded parasite (Pinder et al. Parasit. Today 2000 16:240-245). While multiple proteins appear to be involved in this complex process of RBC invasion, very little is known about the particular role of any individual protein in the process. One of the surface proteins, merozoite surface protein I (MSPI) has been postulated to be involved in the initial interaction of the merozoite with the RBC surface (Holder and Freeman, J. Exp. Med. 1984 160:624-629; Holder et al. Nature 1985 317:270-273; Perkins and Rocco J. Immunol. 1988 141:3190-3196). The localization of this GPI-anchored protein is shared with a number of other GPI-linked proteins including MSP2, MSP4 and MSP5 (Smythe et al. Proc. Natl Acad. Sci. USA 1988 85:5195-5199; Marshall et al. Infect. Immun. 1997 65:4460-4467; Marshall et al. Mol. Biochem. Parasitol. 1998 94:13-25). Apical membrane antigen I (AMA I) is an integral membrane protein that is initially localized to the neck of the rhoptries although it re-distributes onto the surface of the merozoite (Deans et al. Mol. Biochem. Parasitol. 1984 11:189-204; Peterson et al. Mol. Cell Biol. 1989 9:3151-3154; Narum and Thomas Mol. Biochem. 1994 67:59-68; Marshall et al. Mol. Biochem. Parasitol. 1989 27:281-284; Peterson et al. Mol. Cell Biol. 1990 9:3151-3154). The function of AMAI is presently unknown. Within the rhoptries, a number of proteins have been identified that may be involved in the invasion process. These include the rhoptry-associated proteins 1 and 2 (RAP I and RAP2) (Ridley et al. Mol. Biochem. Parasitol. 1990 41:125-134; and Perrin et al. J. Clin. Invest. 1985 75:1718-1721). The soluble complex of these two molecules is delivered out to the rhoptries during invasion and is carried through into the parasitophorous vacuole (Baldi et al. EMBO J. 2000 19:1-9). The erythrocyte-binding antigen 175 (EBA 175) of *Plasmodium falciparum* is located in the micronemes and has been shown to bind to the RBC surface molecule glycophorin A in a sialic acid-dependent manner (Sim et al. Exp. Parasit. 1992 78:259-268; Wu et al. Proc. Natl Acad. Sci. USA 1996 93:1130-1134; Crabb et al. Cell 1997 89:287-296). Disruption of the gene encoding EBA175 to investigate the role of the conserved carboxy-terminal cysteine-rich domain, the transmembrane domain and the cytoplasmic domain suggested these regions were not essential for merozoite invasion (Reed et al. Proc. Natl Acad. Sci USA 2000 97:7509-7514). However, analysis of RBC invasion with these mutants suggested that the EBA175/glycophorinA pathway was disrupted. It appears that the mutant parasites now invaded using a sialic-acid independent pathway suggesting that the parasite has the ability to utilize alternative pathways for invasion of RBCs.

The involvement of an actin-myosin-based motor in invasion was suggested by Miller et al. based upon studies of the effect of cytochalasin B on *Plasmodium* invasion (Miller et al. J. Exp. Med. 1979 149:172-184). In *Plasmodium*, there are two genes for actin. Actin I is intronless and is expressed throughout the parasite life cycle, wherein actin II has an intron and is transcribed only in the sexual stages (Wesseling et al. Mol. Biochem. Parasitol. 1988 27:313-320; Wesseling et al. Mol. Biochem. Parasit. 1988 27:313-320, Wesseling et al. Mol. Biochem. Parasitol. 1989 35:167-176). The amino acid sequence of actin II diverges from previously characterized actins exhibiting only 79% sequence similarity to the sequence of actin I (Wesseling et al. Mol. Biochem. Parasit. 1988 27:313-320). The majority of actin in Apicomplexan parasites appears to be monomeric rather than being in the polymerized form. Localization studies using anti-actin antibodies have indicated that actin is present in the region between the plasma membrane and the inner membrane complex (IMC), which is composed of two closely aligned membranes. The involvement of myosin in Apicomplexan invasion was suggested by Dobrowski et al. and Pinder et al. based upon studies where invasion was reversibly inhibited by the myosin ATPase inhibitor butane-2,3-monoxime (Dobrowski et al. Mol. Microbiol. 1997 26:163-173; Pinder et al. J. Cell Sci. 1998 111:1831-1839). As in other species, *Apicomplexa* contains several myosin genes. Of these, MyoA has been disclosed as rather unique (Heintzehnan and Schwartzman J. Parasitol. 1997 87:429-432). This myosin is expressed in all *Plasmodium* invasive stages. The molecule is very small (approximately 90 kD) but the head domain displays the universally conserved ATP and actin binding sites. MyoA binds actin and actin is released in an ATP-dependent fashion. However, MyoA has several unique features, including virtually no recognizable neck domain (which is normally the binding site for a canonical myosin light chain) and a very short carboxy terminal tail. In the mature merozoite, MyoA is peripherally located with most staining occurring at the apical end and electron microscopy indicates that it is also located between the plasma membrane and the RAC (Pinder et al. J. Cell Sci. 1998 111:1831-1839).

Using a yeast two-hybrid system (Fields and Song Nature 1989 340:245-248; Luban and Goff Curr. Opin. Biotech. 1995 6:59-65), a molecule termed MTIP (MyoA Tail Interacting Protein) was isolated. This molecule binds to the short carboxy terminal tail of MyoA. Studies on the localization of this molecule have led to the proposal of a new model for the organization of the actin-myosin based machinery located between the plasma membrane and the IMC (Bergman et al. J. Cell Sci. 2003 116:39-49). It is believed that the "moving junction" which forms during invasion is a circumferential zone of attachment at the opening of the host cell invagination. This zone is characterized by a markedly thickened host cell membrane with increased electron density and is frequently accompanied by a constriction in the parasite body. The parasite enters the newly forming parasitophorous vacuole by capping the moving junction down its body. Eventually, the parasite becomes enclosed within a cavity delimited by the invaginated host cell membrane (Aikawa et al. J. Cell Bio. 1978 77:72-82; Michel et al. Int. J. Parasitol. 1980 10:309-313). The moving junction is a highly specialized interface of the parasite with the host cell, presumably utilizing cytoskeletal proteins, signaling molecules and receptors. However, very little is known about this interface. The protein MCP-I (Merozoite Capping Protein-1) was localized initially at the attachment site formed between the merozoite apical region and the erythrocyte (Klotz et al. Mol. Biochem. Parasitol. 1989 36:177-185). During the invasion process, MCP-1 migrates around merozoites in an anterior-to-posterior movement to finally persist at the posterior end of the newly invaded parasite (at the end nearest the erythrocyte membrane). MCP-1 is a 415 amino acid protein but interestingly is detected as a 60 kD protein in extracts from blood stage parasites. The amino terminal third of the molecule is an oxido-reductase domain but the function of this domain is not known. Thus, it appears that MCP-1 is localized to the moving junction in invading parasites but its role and potential interactions with other molecules remains unclear, A new protein, *Plasmodium falciparum* Merozoite TRAP-like Invasin 1, referred to herein as PfMTI-1, has now been isolated and characterized. Blockage or inhibition of this protein is believed to prevent the malaria parasite from invading red blood cells, thus preventing or lessening the clinical severity of the disease. This protein and homologs or orthologs thereof serve as prime targets for immunologic and chemotherapeutic intervention.

SUMMARY OF THE INVENTION

An aspect of the present invention relates to an isolated protein referred to herein as PfMTI-1, of the malaria parasite *Plasmodium falciparum* and homologs or orthologs thereof that interact with a red blood cell to be invaded by the parasite and link with a component of the actin-myosin based machinery of the malaria parasite.

Another aspect of the present invention relates to isolated nucleic acid sequences encoding the protein PfMTI-1 of the malaria parasite *Plasmodium falciparum* and homologs or orthologs thereof that interact with a red blood cell to be invaded by the parasite and link with a component of the actin-myosin based machinery of the malaria parasite.

Another aspect of the present invention relates to isolated antibodies which specifically bind the protein PfMTI-1 or a homolog or ortholog thereof, or a fragment thereof.

Another aspect of the present invention relates to a method for identifying potential therapeutic agents for malaria which comprises assessing the ability of a potential therapeutic agent to inhibit the function of the PfMTI-1 protein or a homolog or ortholog thereof thereby inhibiting the interaction of this protein with a red blood cell to be invaded by the malaria parasite and/or its linkage to a component of the actin-myosin based machinery of the malaria parasite.

Another aspect of the present invention relates to compositions and methods for inhibiting or preventing invasion of red blood cells by a malaria parasite. Compositions of the present invention comprise an agent which inhibits interaction of PfMTI-1 or an ortholog thereof with a host red blood cell and/or linkage to a component of actin-myosin based machinery of the malaria parasite. Methods of the present invention comprise administering this composition as a chemotherapeutic agent to a subject infected with a malaria parasite or as an immunologic agent to prevent infection in subjects at risk for infection by a malaria parasite.

Description of the Sequence Listing

SEQ ID NO: 1 and SEQ ID NO:2 are the amino acid sequence and the nucleic acid sequence, respectively, of PfMTI-1 isolated from *Plasmodium falciparum* strain 3D7.

SEQ ID NO:3 and SEQ ID NO:4 are the amino acid sequence and the nucleic acid sequence, respectively, of PfMTI-1 isolated from *Plasmodium falciparum* strain FVO.

SEQ ID NO:5 and SEQ ID NO:6 are the amino acid sequence and the nucleic acid sequence, respectively, of PfMTI-1 from *Plasmodium falciparum* strain D10.

SEQ ID NO:7 and SEQ ID NO:8 are the amino acid sequence and the nucleic acid sequence, respectively, of PfMTI-1 isolated from *Plasmodium falciparum* strain HB3.

SEQ ID NO:9 and SEQ ID NO:10 are the amino acid sequence and the nucleic acid sequence, respectively, of PfMTI-1 isolated from *Plasmodium falciparum* strain M24.

SEQ ID NO: 11 and SEQ ID NO: 12 are the amino acid sequence and the nucleic acid sequence, respectively, of PfMTI-1 isolated from *Plasmodium falciparum* strain MCAMP.

SEQ ID NO: 13 and SEQ ID NO: 14 are the amino acid sequence and the nucleic acid sequence, respectively, of PfMTI-1 isolated from *Plasmodium falciparum* strain C2A.

SEQ ID NO: 15 is an orthologous amino acid sequence to PfMTI-1 isolated from *Plasmodium vivax*.

SEQ ID NO: 16 an orthologous amino acid sequence to PfMTI-1 isolated from *Plasmodium knowlesi*.

DETAILED DESCRIPTION OF THE INVENTION

All invasive forms of the human malaria parasite (*Plasmodium falciparum*) must have a protein that serves as a molecular bridge or link between the host cell that is being invaded and the motor machinery of the parasites that drives the invasion process. The bridging or linking protein of the merozoite, the invasive form of the asexual or blood stage of the parasite life cycle that interacts with the red blood cell to be invaded and links with a component of the actin-myosin based motor machinery of the parasite has now been identified. Exemplary amino acid sequences of this protein, *Plasmodium falciparum* Merozoite TRAP-like Invasion 1, referred to herein as PfMTI-1, are depicted in SEQ ID NO: 1, 3, 5, 7, 9, 11 and 13. SEQ ID NO: 1 is the amino acid sequence of the protein isolated from *P. falciparum* strain 3D7. SEQ ID NO:3 is the amino acid sequence of the protein isolated from *P. falciparum* strain FVO. SEQ ID NO:5 is the amino acid sequence of the protein isolated from *P. falciparum* strain D10. SEQ ID NO:7 is the amino acid sequence of the protein isolated from *P. falciparum* strain HB3. SEQ ID NO:9 is the amino acid sequence of the protein isolated from *P. falciparum* strain M24. SEQ ID NO: 11 is the amino acid sequence of the protein isolated from *P. falciparum* strain MCAMP. SEQ ID NO: 13 is the amino acid sequence of the protein isolated from *P. falciparum* strain C2A. Nucleic acid sequences encoding the PfMTI-1 protein of strains 3D7, FVO, D10, HB3, M24, MCAMP and C2A are depicted in SEQ ID NO:2, 4, 6, 8, 10, 12 and 14, respectively.

This protein was identified using a bioinformatic approach to search for blood stage receptors in a *P. falciparum* predicted gene product database. Search criteria used allowed for the presence of an additional trans-membrane domain (signal sequence and two trans-membrane domains) as the computer can predict a trans-membrane domain from merely a stretch of hydrophobic domains. Only 6 proteins of *P. falciparum* met all criteria, one of which is PfMTI-1.

PfMTI-1 of the various strains comprises 488 to 503 amino acids and contains a signal sequence, a single transmembrane domain, a thrombospondin domain and an acidic cytoplasmic domain with a tryptophan residue near the carboxy-terminus (residue 495 of 3D7). Using microarray data, PfMTI-1 was identified as being expressed in late stage parasites. Further, examination of other genes with a similar pattern of expression revealed that PfMTI-1 is expressed at the same approximate time during the parasite cell cycle as other molecules involved in the invasion process, such as PfMYOA (*Plasmodium falciparum* Myosin A, Pinder et al, J. Cell Sci. 2000 111:1831-1839), PfMTIP (*Plasmodium falciparum* Myosin A Tail Interacting Protein, Bergman et al. J. Cell Sci. 2003 116:39-49) and PfAMA1 (*Plasmodium falciparum* Apical Membrane Antigen 1, Hodder et al, Infect. Immun. 2001 69:3286-3294). It is believed that this protein serves as the molecular bridge or link between a host erythrocyte being invaded by the malaria parasite and the motor machinery of the malaria parasite that drives the infection process.

The carboxy-terminal 44 amino acids of PfMTI-1 are expressed as a histidine-tagged recombinant protein and are incubated in an in vitro binding assay with recombinant Pf Aldolase (expressed as a glutathione-S-transferase fusion protein). The binding of the GST-aldolase fusion to the PfMTI-1 protein is specifically detected by incubation with an antibody directed against the GST moiety of the fusion protein and subsequent incubation with a conjugation secondary antibody. Furthermore, the specificity of the binding to Pf aldolase has been demonstrated using a similar histidine-tagged PfMTI-1 recombinant protein containing a tryptophan→alanine change at the fourth position from the carboxy-terminus of PfMTI-1. This result implicates PfMTI-1 as being a link between the plasma membrane of the parasite and the actin-myosin motor required for the invasion of red blood cells. This link between PfMTI-1 and Pf actin is indirect via the bridging molecule, Pf aldolase. Thus, inhibition of the function of the extracellular domain of PfMTI-1 or the interaction between PfMTI-1 and Pf aldolase may block the ability of the parasite to invade red blood cells.

Thus, the present invention provides an isolated malaria protein, PfMTI-1, and isolated homologs or orthologs thereof, now characterized as functioning as the molecular bridge or link between a host red blood cell that is being invaded and the motor machinery of the parasite that drives the invasion process. The amino acid sequence of exemplary PfMTI-1 proteins of the present invention which function as the molecular bridge or link between a host red blood cell that is being invaded and the motor machinery of the parasite that drives the invasion process are depicted in SEQ ID NO: 1, 3, 5, 7, 9, 11 and 13.

Based upon these exemplary amino acid sequences and the activity now taught herein for this protein, those skilled in the art can now routinely identify variant amino acid sequences, homologous or orthologous amino acid sequences and fragments of this exemplary amino acid sequence as well as fragments of variant and homologous or orthologous amino acid sequences exhibiting similar binding capabilities and/or activities with respect to host red blood cells and/or a component of the actin-myosin based motor machinery of the malaria parasite. Using such techniques, the inventors have identified orthologous proteins in *P. vivax* (SEQ ID NO:15) and *P. knowlesi* (SEQ ID NO:16).

The present invention also provides isolated nucleic acid sequences encoding PfMTI-1 and isolated homologs or orthologs, or fragments thereof. Exemplary nucleic acid sequences encoding PfMTI-1 are depicted in SEQ ID NO: 2, 4, 6, 8, 10, 12 and 14. As will be understood by those skilled in the art, however, due to degeneracy in the genetic code, additional nucleic acid sequences may encode this protein. Identification of these degenerative sequences can be performed routinely by those skilled in the art based upon the teachings herein. Accordingly, these additional degenerate nucleic acid sequences as well as isolated nucleic acid sequences encoding homologs or orthologs of PfMTI-1 are also encompassed within the scope of this invention.

By the term "isolated", as used herein, it is meant a protein or fragment thereof, or a nucleic acid sequence that is (1) no longer associated with naturally associated components that accompany it in its native state, (2) is free of other proteins or nucleic acid sequences from the same species (3) is expressed by a cell from a different species, or (4) does not occur in nature. Thus, a protein or fragment or nucleic acid sequence that is chemically synthesized or synthesized in a cellular system different from the cell from which it naturally originates will be "isolated" from its naturally associated components. A protein or fragment thereof or a nucleic acid sequence may also be rendered substantially free of naturally associated components by isolation, using protein or nucleic acid sequence purification techniques well-known in the art.

By "homolog" or "homologous" when referring to a protein of the present invention it is meant proteins from different organisms with a similar sequence to the encoded amino acid sequence of PfMTI-1 and a similar biological activity or function. Although two proteins are said to be "homologous," this does not imply that there is necessarily an evolutionary relationship between the proteins. Instead, the term "homologous" is defined to mean that the two proteins have similar amino acid sequences and similar biological activities or functions. In a preferred embodiment, a homologous protein is one that exhibits 50% sequence similarity to PfMTI-1, preferred is 60% sequence similarity, more preferred is 70% sequence similarity. Even more preferred are homologous proteins that exhibit 80%, 85% or 90% sequence similarity to PfMTI-1. In a yet more preferred embodiment, a homologous protein exhibits 95%, 97%, 98% or 99% sequence similarity.

Most preferred is an ortholog or orthologous protein, meaning that the homologous proteins have a common ancestral species.

The term "fragment" as used herein with respect to proteins of the present invention refers to a polypeptide that has an amino-terminal and/or carboxy-terminal deletion compared to the full-length PfMTI-1 protein or a homolog or ortholog thereof. In a preferred embodiment, the fragment is a contiguous sequence in which the amino acid sequence of the fragment is identical to the corresponding positions in the naturally-occurring PfMTI-1 protein, or homolog or ortholog thereof. Fragments typically are at least 5, 6, 7, 8, 9 or 10 amino acids long, preferably at least 12, 14, 16 or 18 amino acids long, more preferably at least 20 amino acids long, more preferably at least 25, 30, 35, 40 or 45, amino acids, even more preferably at least 50 or 60 amino acids long, and even more preferably at least 70 amino acids long. Most preferably, the fragment is of sufficient length to mimic the binding capability and/or activities of the full length protein.

The present invention also relates to derivatives of the PfVN-291 protein and homologues, orthologues and fragments thereof A "derivative" when used herein with respect to proteins of the present invention refers to a modified protein substantially similar in primary structural sequence to PfMTI-1 or a homolog or ortholog thereof but which includes, e.g., in vivo or in vitro chemical and biochemical modifications that are not found in the naturally occurring proteins. Examples of such modifications include, but are in no way limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. Other modifications include, for example, labeling with a detectable label such as a radionuclide, a fluorophore or an enzyme.

The present invention also provides isolated antibodies which specifically bind PfMTI-1 or a homolog or ortholog thereof or a fragment of PfMTI-1 or a homolog or ortholog thereof. The term "antibody" as used herein refers to an intact immunoglobulin, or to an antigen-binding portion of an immunoglobulin that competes with the intact antibody for specific binding to a protein or fragment of a protein of the present invention. Antigen-binding portions of an immunoglobulin of the present invention can be produced by various techniques including, but not limited to recombinant DNA techniques and enzymatic or chemical cleavage of intact antibodies. Exemplary antigen-binding portions include Fab, Fab', F(ab')$_2$, Fv, dAb, and complementarity determining region (CDR) fragments, single-chain antibodies (scFv), chimeric antibodies, diabodies and polypeptides that contain at least a portion of an immunoglobulin that is sufficient to confer specific antigen binding to the polypeptide. Fab fragments are monovalent fragments consisting of VL, VH, CL and CH1 domains. F(ab')$_2$ fragments are bivalent fragments comprising two Fab fragments linked by a disulfide bridge at the hinge region. Fd fragments comprise a VH and CH1 domain. Fv fragment comprise a VL and VH domain of a single arm of an antibody. dAb fragments comprise a VH domain (Ward et al., Nature 1989 341: 544-546).

Antibodies of the present invention may be single-chain antibodies (scFv), meaning an antibody in which VL and VH regions are paired to form a monovalent molecule via a synthetic linker that enables them to be made as a single protein chain (Bird et al., Science 1988 242: 423-426; Huston et al., Proc. Natl. Acad. Sci. USA 1988 85: 5879-5883). Antibodies of the present invention may also be diabodies, meaning bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (Holliger et al., Proc. Natl. Acad. Sci. USA 1993 90: 6444-6448; Poljak et al. 1994 Structure 2: 1121-1123). Further, one or more CDRs can be incorporated into a molecule either covalently or noncovalently to produce an immunoadhesin. An immunoadhesin may incorporate the CDR(s) as part of a larger polypeptide chain, may covalently link the CDR(s) to another polypeptide chain, or may incorporate the CDR(s) noncovalently. The CDRs permit the immunoadhesin to specifically bind to a particular antigen of interest, in this case PfMTI-1 or a homolog or ortholog thereof. A chimeric antibody is an antibody that contains one or more regions from one antibody and one or more regions from one or more other antibodies.

An "isolated antibody" as used herein is an antibody that (1) is not associated with naturally-associated components, including other naturally-associated antibodies, that accompany it in its native state, (2) is free of other proteins from the same species, (3) is expressed by a cell from a different species, or (4) does not occur in nature. It is known that purified proteins, including purified antibodies, may be stabilized with non-naturally-associated components. The non-naturally-associated component may be a protein, such as albumin (e.g., BSA) or a chemical such as polyethylene glycol (PEG).

By "bind specifically" and "specific binding" as used herein it is meant the ability of an antibody of the present invention to bind to a first molecular species in preference to binding to other molecular species with which the antibody and first molecular species are admixed. An antibody is said specifically to "recognize" a first molecular species when it can bind specifically to that first molecular species. In the present invention the first molecular species comprises PfMTI-1 or a homolog or ortholog thereof or a fragment of PfMTI-1 or a homolog or ortholog thereof.

Identification of PfMTI-1 and homologs and orthologs thereof can be used to design and/or identify therapeutic agents which prevent infection by malaria parasites and/or decrease the severity of clinical.

For example, the structure of these proteins can be used in computer modeling programs to design mimetics of PfMTI-1 and homologs or orthologs thereof. By "mimetic" it is meant to include peptide based compounds, also referred to as peptidomimetics, as well as small organic molecules. Preferably mimetics of the present invention are designed to bind to either the erythrocyte binding site of PfMTI-1 or the component of the actin-myosin based motor machinery of the malaria parasite to which PfMTI-1 binds, thereby inhibiting the ability of PfMTI-1 or homologs or orthologs thereof to form a molecular bridge between red blood cells and the parasite.

Identification of PfMTI-1 and its function can also be used in the development of high throughput screening assays to identify potential chemotherapeutic agents which inhibit the function of this protein and orthologs or homologs thereof, thereby decreasing severity of the clinical symptoms of malaria infections. In vitro binding assays, in a high throughput format could be developed to screen for agents that disrupt or prevent the binding of PfMTI-1 to parasite aldolase. These agents would then be screen in culture for their effect on the in vivo growth or invasion of *Plasmodium falciparum*. Alternatively, an agent may be isolated that blocks the presumptive interaction between PfMTI-1 and a component on the surface of the red cell. Again, similar assay would be utilized to screen the efficacy of the agent in vivo.

Further, this protein and homologs or orthologs thereof serve as prime targets for vaccine development against malaria infection. A useful vaccine will comprise an antigen capable of invoking an immune response against the PfMTI-1 protein or an ortholog or homolog thereof. Exemplary antigens include, but are not limited to the entire PfMTI-1 sequence, the exocellular domain of PfMTI-1, or regions thereof.

Thus, the present invention also provides methods for identifying potential therapeutic agents for malaria which comprises assessing the ability of a potential therapeutic to inhibit the function of the PfMTI-1 protein or an ortholog or homolog thereof thereby inhibiting the interaction of this protein with a red blood cell to be invaded by the malaria parasite and/or its linkage to a component of the actin-myosin based machinery of the malaria parasite. Agents may inhibit the function directly by acting on the protein or protein's binding site or indirectly by invoking an immune response against the protein.

Further, agents identified as inhibiting the function of the PfMTI-1 protein or an ortholog or homolog thereof are expected to be useful in inhibiting and/or preventing malaria infections. Thus, the present invention also provides compositions and methods for inhibiting or preventing invasion of red blood cells by a malaria parasite.

Compositions of the present invention comprise an agent, which inhibits interaction of PfMTI-1 or an ortholog or homolog thereof with a host red blood cell and/or linkage to a component of actin-myosin based machinery of the malaria parasite in a pharmaceutically acceptable carrier. Selection of a pharmaceutically acceptable carrier for use in these compositions can be performed routinely by those of skill in the art based upon the solubility characteristics of the agent, its mode of action and the mode of administration desired for the composition. For example, if the agent is a vaccine typically administered via intramuscular injection, the carrier may comprise a sterile aqueous vehicle such as sterile saline or sterile phosphate buffered saline and may further comprise an adjuvant to enhance immunogenicity such as alum adjuvant or other adjuvants approved for human use.

Compositions of the present may be administered as a chemotherapeutic agent to a subject infected with a malaria parasite to prevent or decrease clinical severity of the infection. Alternatively, compositions of the present invention may be administered as immunologic agents to prevent or inhibit infection in subjects at risk for infection by a malaria parasite.

What is claimed is:

1. An isolated fragment of the full-length *Plasmodium falciparum* Merozoite TRAP-like Invasin 1 (PfMTI-1) protein, the fragment comprising the final 44 amino acids of the carboxy-terminus of the PfMTI-1 protein,
   wherein the amino acid sequence of the PfMTI-1 protein is selected from the group consisting of SEQ ID NO: 1, SEQ ID NO: 3, SEQ ID NO: 5, SEQ ID NO: 11 and SEQ ID NO: 13,
   wherein the fragment functions as a link or bridge between a host red blood cell that is being invaded by *Plasmodium falciparum* and the actin-myosin based motor machinery of the *Plasmodium falciparum* that drives the invasion process of the cell by the *Plasmodium falciparum*.

* * * * *

SEQUENCE LISTING

<160> NUMBER OF SEQ ID NOS: 16

<210> SEQ ID NO 1
<211> LENGTH: 498
<212> TYPE: PRT
<213> ORGANISM: Plasmodium falciparum strain 3D7

<400> SEQUENCE: 1

```
Met Lys Lys Thr Ile Leu Asn Leu Tyr Leu Ile Asn Ile Leu Phe Ala
1               5                   10                  15

Leu Ser Asp Val Lys Gly Ile Ser Thr His Asp Thr Cys Asp Glu Trp
            20                  25                  30

Ser Glu Trp Ser Ala Cys Thr His Gly Ile Ser Thr Arg Lys Cys Leu
        35                  40                  45

Ser Asp Ser Ser Ile Lys Asp Glu Thr Leu Val Cys Thr Lys Cys Asp
    50                  55                  60

Lys Trp Gly Glu Trp Ser Glu Cys Lys Asp Gly Arg Met His Arg Lys
65                  70                  75                  80

Val Leu Asn Cys Pro Phe Ile Lys Glu Glu Gln Glu Cys Asp Val Asn
                85                  90                  95

Asn Glu Met Ala Glu Asp Thr His Met Asn Asn Ser Tyr Ile Tyr Phe
            100                 105                 110

Asn Ala Asp Asp Gly Asp Asn Glu Tyr Glu Asp His Asp Asp Lys Asn
        115                 120                 125

Asp Asp Asp Lys Asn Tyr Asp Asn Glu Asn Asp Asp Lys Asn Asp
    130                 135                 140

Asp Asp Lys Asn Asp Asp Lys Asn Asp Asp Lys Asn Asp Asp
145                 150                 155                 160

Asp Lys Asn Asp Asp Glu Glu Asn Tyr Asn Asp Thr Glu Glu Lys Val
                165                 170                 175

Lys Asn Asn Asp Ile His Asn Ser Ser Ala Asn Ser Asn Glu Val
            180                 185                 190

Thr Asn Phe Ile Gln Ile Lys Asp Lys Ile Met Ile Lys His Lys Thr
        195                 200                 205

Thr Asn Ile His Pro Val Asn Phe Ile Gln Glu Lys Tyr Thr Arg Asn
    210                 215                 220

Asn Lys Tyr Arg Ser Asp Asn Phe Ser Lys Ile Leu Asn Asn Met Asn
225                 230                 235                 240

His Ile Asn Asn Asn Tyr Asn Ser Arg Ser Ser Ser Thr Ser Ser
                245                 250                 255

Lys Asn Ala Arg Gly Tyr Arg Gly Ser Ser Asn Met Tyr Pro His
            260                 265                 270

Val Pro Asn Tyr Thr Ser Ser Val His Asn Ser Thr Asn Asn Glu
        275                 280                 285

Arg Lys Ser Asp Glu Asp Leu Asn Ile Glu Gly Asp Asn Ile Thr
    290                 295                 300

Lys Glu Glu Arg Ile Val Pro Ile Asn Asn Lys Asn Tyr Asp Asn His
305                 310                 315                 320

Asp Glu His Ser Asn Ile His Glu His Asp Thr Ser Arg Asn Val Asp
                325                 330                 335

Asn Glu Lys Tyr Asn Ser Asn Asp Asp Leu Pro Asn Leu Ser Thr Tyr
            340                 345                 350

Asp Tyr Asp Met Asn Asn Asp Ser Tyr Lys Lys Asn His Met Lys Lys
        355                 360                 365
```

```
Pro Met Asp Ser Ile Lys Glu Glu Gln Thr Lys Gln Glu Asn Asn Gln
    370                 375                 380

Asn Asn Glu Lys Val Ser Ser Glu Lys Gln Asn Asp Asp Ile Ser
385                 390                 395                 400

Ala Leu Tyr Glu His Met Asn Thr Lys Asp Gln Glu His Thr Gln His
                405                 410                 415

Glu Gln Pro Asn Asp Ser Ala His Gly His Phe Glu Asp Tyr Ser Lys
                420                 425                 430

Leu Tyr Ile Ala Ser Gly Val Ala Thr Leu Val Leu Leu Gly Gly Ser
                435                 440                 445

Ile Thr Phe Tyr Phe Leu Arg Lys Glu Lys Thr Glu Lys Val Val Gln
    450                 455                 460

Glu Glu Thr Lys Glu Glu Asn Phe Glu Val Met Phe Asn Asp Asp Ala
465                 470                 475                 480

Leu Lys Gly Lys Asp Asn Lys Ala Met Asp Glu Glu Glu Phe Trp Ala
                485                 490                 495

Leu Glu

<210> SEQ ID NO 2
<211> LENGTH: 1497
<212> TYPE: DNA
<213> ORGANISM: Plasmodium falciparum strain 3D7

<400> SEQUENCE: 2
atgaagaaaa caatactaaa tttatatttg ataaatatat tatttgcctt atctgacgta     60
aaaggtatat caacacatga tacatgcgat gaatggtcag aatggtctgc atgtactcat    120
ggaatcagta ccaggaaatg tttaagtgat tcttctatta aggatgagac acttgtatgt    180
acaaatgtg ataatgggg agaatggtca gaatgtaaag atgggagaat gcatagaaaa      240
gttttgaatt gtcctttttat taagaagaa caagaatgtg atgtaaataa tgaaatggcg    300
gaggacacac atatgaataa tagctatata tatttcaacg cagatgatgg tgataatgaa    360
tatgaagatc atgatgataa aaatgatgat gataaaaatt atgataatga aaatgatgat    420
gataaaaatg atgatgataa aaatgatgat gataaaaatg atgatgataa aaatgatgat    480
gataaaaatg atgatgagga aaattataat gatactgaag aaaaggtaaa aaataatgat    540
atacataatt ctagtgctaa tagtaataat gaggttacta atttcataca gataaaaagat    600
aaaattatga ttaaacataa acaacaaat atacatccag tgaattttat acaagaaaaa    660
tatacaagaa ataataaata tagatctgat aatttttcta aaatattaaa taacatgaat    720
catataaata ataataatta taatagtaga agtagtagta cttcttcgaa aaatgctaga    780
ggttatagag gaggaagcag taatatgtat ccacatgtac caaattacac gagttccttct    840
gtacataata gtacaaataa tgaaagaaaa agtgatgaag acttggataa tatagagggt    900
gataatataa ctaaagaaga aaggattgtt ccaataaaata acaaaaatta tgataatcat    960
gatgaacata gtaatataca cgagcatgat acatctcgta atgtagataa tgaaaaatat   1020
aattcaaatg atgatttacc aaacttgtcg acttatgatt atgatatgaa taatgattct   1080
tataaaaaga atcacatgaa aaaacctatg gattctatta agaagaaca acaaaaacaa   1140
gaaaataatc agaacaatga aaagtatcc tcctcagaaa acaaaatga tgatatatct   1200
gcattatatg aacatatgaa taccaaggat caagagcata cacaacatga acaaccaaat   1260
gacagtgcac atggtcactt tgaagattac agtaaattat atattgctag tggtgtagct   1320
actcttgtac tcttgggagg aagtataact ttctatttct tacgtaaaga aaaaacagaa   1380
```

```
aaagttgtac aagaagaaac aaaagaggaa aactttgaag tcatgtttaa tgatgatgct   1440
ctcaagggaa aggataacaa agctatggat gaagaagaat tctgggcact cgaatga      1497
```

<210> SEQ ID NO 3
<211> LENGTH: 488
<212> TYPE: PRT
<213> ORGANISM: Plasmodium falciparum strain FVO

<400> SEQUENCE: 3

```
Met Lys Lys Thr Ile Leu Asn Leu Tyr Leu Ile Asn Ile Leu Phe Ala
1               5                   10                  15

Leu Ser Asp Val Lys Gly Ile Ser Thr His Thr Cys Asp Glu Trp
            20                  25                  30

Ser Glu Trp Ser Ala Cys Thr His Gly Ile Ser Thr Arg Lys Cys Leu
        35                  40                  45

Ser Asp Ser Ser Ile Lys Asp Glu Thr Leu Val Cys Thr Lys Cys Asp
    50                  55                  60

Lys Trp Gly Glu Trp Ser Glu Cys Lys Asp Gly Arg Met His Arg Lys
65                  70                  75                  80

Val Leu Asn Cys Pro Phe Ile Lys Glu Glu Gln Glu Cys Asp Val Asn
                85                  90                  95

Asn Glu Met Ala Glu Asp Thr His Met Asn Asn Ser Tyr Ile Tyr Phe
            100                 105                 110

Asn Ala Asp Asp Gly Asp Asn Glu Tyr Glu Asp His Asp Asp Lys Asn
        115                 120                 125

Asp Asp Asp Lys Asn Tyr Asp Asn Glu Asn Asp Asp Lys Asn Asp
    130                 135                 140

Asp Asp Lys Asn Asp Asp Lys Asn Asp Glu Glu Asn Tyr Asn
145                 150                 155                 160

Asp Thr Glu Glu Lys Val Lys Asn Asn Asp Ile His Asn Ser Ser Ala
                165                 170                 175

Asn Ser Asn Asn Glu Val Thr Asn Phe Ile Gln Ile Lys Asp Lys Ile
            180                 185                 190

Met Ile Lys His Lys Thr Thr Asn Ile His Pro Val Asn Phe Ile Gln
        195                 200                 205

Glu Lys Tyr Thr Arg Asn Asn Lys Tyr Arg Ser Asp Asn Phe Ser Lys
    210                 215                 220

Ile Leu Asn Asn Met Asn His Ile Asn Asn Asn Tyr Asn Ser Arg
225                 230                 235                 240

Ser Ser Ser Thr Ser Ser Lys Asn Ala Arg Gly Tyr Arg Gly Gly Ser
                245                 250                 255

Ser Asn Met Tyr Pro His Val Pro Asn Tyr Thr Ser Ser Ser Val His
            260                 265                 270

Asn Ser Thr Asn Asn Glu Arg Lys Ser Asp Glu Asp Leu Asp Asn Ile
        275                 280                 285

Glu Gly Asp Asn Ile Thr Lys Glu Glu Arg Ile Val Pro Ile Asn Asn
    290                 295                 300

Lys Asn Tyr Asp Asn His Asp Glu His Ser Asn Ile His Glu His Asp
305                 310                 315                 320

Thr Ser Arg Asn Val Asp Asn Glu Lys Tyr Asn Ser Asn Asp Asp Leu
                325                 330                 335

Pro Asn Leu Ser Thr Tyr Asp Tyr Asp Met Asn Asp Ser Tyr Lys
            340                 345                 350
```

```
Lys Asn His Met Lys Lys Pro Met Asp Ser Ile Lys Glu Glu Gln Thr
            355                 360                 365
Lys Gln Glu Asn Asn Gln Asn Asn Glu Lys Val Ser Ser Ser Glu Lys
    370                 375                 380
Gln Asn Asp Asp Ile Ser Ala Leu Tyr Glu His Met Asn Thr Lys Asp
385                 390                 395                 400
Gln Glu His Thr Gln His Glu Gln Thr Asn Asp Ser Ala His Gly His
                405                 410                 415
Phe Glu Asp Tyr Ser Lys Leu Tyr Ile Ala Ser Gly Val Ala Thr Leu
            420                 425                 430
Val Leu Leu Gly Gly Ser Ile Thr Phe Tyr Phe Leu Arg Lys Glu Lys
            435                 440                 445
Thr Glu Lys Val Val Gln Glu Glu Thr Lys Glu Glu Asn Phe Glu Val
            450                 455                 460
Met Phe Asn Asp Asp Ala Leu Lys Gly Lys Asp Asn Lys Ala Met Asp
465                 470                 475                 480
Glu Glu Glu Phe Trp Ala Leu Glu
            485
```

<210> SEQ ID NO 4
<211> LENGTH: 1467
<212> TYPE: DNA
<213> ORGANISM: Plasmodium falciparum strain FVO

<400> SEQUENCE: 4

```
atgaagaaaa caatactaaa tttatatttg ataaatatat tatttgcctt atctgacgta      60
aaaggtatat caacacatga tacatgcgat gaatggtcag aatggtctgc atgtactcat     120
ggaatcagta ccaggaaatg tttaagtgat tcttctatta aggatgagac acttgtatgt     180
acaaaatgtg ataaatgggg agaatggtca gaatgtaaag atgggagaat gcatagaaaa     240
gttttgaatt gtccttttat taaagaagaa caagaatgtg atgtaaataa tgaaatggcg     300
gaggacacac atatgaataa tagctatata tatttcaacg cagatgatgg tgataatgaa     360
tatgaagatc atgatgataa aaatgatgat gataaaaatt atgataatga aaatgatgat     420
gataaaaatg atgatgataa aaatgatgat gaaaaaatg atgatgagga aaattataat     480
gatactgaag aaaaggtaaa aaataatgat atacataatt ctagtgctaa tagtaataat     540
gaggttacta atttcataca gataaaagat aaaattatga ttaaacataa aacaacaaat     600
atacatccag tgaattttat acaagaaaaa tatacaagaa ataataaata tagatctgat     660
aatttttcta aaatattaaa taacatgaat catataaata ataataatta taatagtaga     720
agtagtagta cttcttcgaa aaatgctaga ggttatagag gaggaagcag taatatgtat     780
ccacatgtac caaattacac gagttcttct gtacataata gtacaaataa tgaaagaaaa     840
agtgatgaag acttggataa tatagagggt gataatataa ctaagaagaa aggattgtt      900
ccaataaata acaaaaatta tgataatcat gatgaacata gtaatataca cgagcatgat     960
acatctcgta atgtagataa tgaaaaatat aattcaaatg atgatttacc aaacttgtcg    1020
acttatgatt atgatatgaa taatgattct tataaaaaga atcacatgaa aaacctatg     1080
gattctatta agaagaaaca acaaaaacaa gaaataatc agaacaatga aaaagtatcc     1140
tcctcagaaa acaaaaatga tgatatatct gcattatatg aacatatgaa taccaaggat    1200
caagagcata cacaacatga acaaacaaat gacagtgcac atggtcactt tgaagattac    1260
agtaaattat atattgctag tggtgtagct actcttgtac tcttgggagg aagtataact    1320
```

```
ttctatttct tacgtaaaga aaaaacagaa aaagttgtac aagaagaaac aaaagaggaa    1380
aactttgaag tcatgtttaa tgatgatgct ctcaagggaa aggataacaa agctatggat    1440
gaagaagaat tctgggcact cgaatga                                         1467
```

<210> SEQ ID NO 5
<211> LENGTH: 493
<212> TYPE: PRT
<213> ORGANISM: Plasmodium falciparum strain D10

<400> SEQUENCE: 5

```
Met Lys Lys Thr Ile Leu Asn Leu Tyr Leu Ile Asn Ile Leu Phe Ala
1               5                   10                  15

Leu Ser Asp Val Lys Gly Ile Ser Thr His Asp Thr Cys Asp Glu Trp
            20                  25                  30

Ser Glu Trp Ser Ala Cys Thr His Gly Ile Ser Thr Arg Lys Cys Leu
        35                  40                  45

Ser Asp Ser Ser Ile Lys Asp Glu Thr Leu Val Cys Thr Lys Cys Asp
    50                  55                  60

Lys Trp Gly Glu Trp Ser Glu Cys Lys Asp Gly Arg Met His Arg Lys
65                  70                  75                  80

Val Leu Asn Cys Pro Phe Ile Lys Glu Glu Gln Glu Cys Asp Val Asn
                85                  90                  95

Asn Glu Met Ala Glu Asp Thr His Met Asn Asn Ser Tyr Ile Tyr Phe
            100                 105                 110

Asn Ala Asp Asp Gly Asp Asn Glu Tyr Glu Asp His Asp Asp Lys Asn
        115                 120                 125

Asp Asp Asp Lys Asn Tyr Asp Asn Glu Asn Asp Asp Lys Tyr Asp
    130                 135                 140

Asp Asp Lys Asn Asp Asp Lys Asn Asp Asp Lys Asn Asp Asp
145                 150                 155                 160

Glu Glu Asn Tyr Asn Asp Thr Glu Glu Lys Val Lys Asn Asn Asp Ile
                165                 170                 175

His Asn Ser Ser Ala Asn Ser Asn Asn Glu Val Thr Asn Phe Ile Gln
            180                 185                 190

Ile Lys Asp Lys Ile Met Ile Lys His Lys Thr Thr Asn Ile His Pro
        195                 200                 205

Val Asn Phe Ile Gln Glu Lys Tyr Thr Arg Asn Asn Lys His Arg Ser
    210                 215                 220

Asp Asn Phe Ser Lys Ile Leu Asn Asn Met Asn His Ile Asn Asn
225                 230                 235                 240

Asn Tyr Asn Ser Arg Ser Ser Thr Ser Ser Lys Asn Ala Arg Gly
                245                 250                 255

Tyr Arg Gly Gly Ser Ser Asn Met Tyr Pro His Val Pro Asn Tyr Thr
            260                 265                 270

Ser Ser Ser Val His Asn Ser Thr Asn Asn Glu Arg Lys Ser Asp Glu
        275                 280                 285

Asp Leu Asp Asn Ile Glu Gly Asp Asn Ile Thr Lys Glu Glu Arg Ile
    290                 295                 300

Val Pro Ile Asn Asn Lys Asn Tyr Asp Asn His Asp Glu His Ser Asn
305                 310                 315                 320

Ile His Glu His Asp Thr Ser Arg Asn Val Asp Asn Glu Lys Tyr Asn
                325                 330                 335

Ser Asn Asp Asp Leu Pro Asn Leu Ser Thr Tyr Asp Tyr Asp Met Asn
            340                 345                 350
```

```
Asn Asp Ser Tyr Lys Lys Asn His Met Lys Lys Pro Met Asp Ser Ile
        355                 360                 365

Lys Glu Glu Gln Thr Lys Gln Glu Asn Asn Gln Asn Asn Glu Lys Val
    370                 375                 380

Ser Ser Ser Glu Lys Gln Asn Asp Asp Ile Ser Ala Leu Tyr Glu His
385                 390                 395                 400

Met Asn Thr Lys Asp Gln Glu His Thr Gln His Glu Gln Pro Asn Asp
                405                 410                 415

Ser Ala His Gly His Phe Glu Asp Tyr Ser Lys Leu Tyr Ile Ala Ser
            420                 425                 430

Gly Val Ala Thr Leu Val Leu Leu Gly Gly Ser Ile Thr Phe Tyr Phe
                435                 440                 445

Leu Arg Lys Glu Lys Thr Glu Lys Val Val Gln Glu Glu Thr Lys Glu
        450                 455                 460

Glu Asn Phe Glu Val Met Phe Asn Asp Asp Ala Leu Lys Gly Lys Asp
465                 470                 475                 480

Asn Lys Ala Met Asp Glu Glu Glu Phe Trp Ala Leu Glu
                485                 490

<210> SEQ ID NO 6
<211> LENGTH: 1482
<212> TYPE: DNA
<213> ORGANISM: Plasmodium falciparum strain D10

<400> SEQUENCE: 6
atgaagaaaa caatcctaaa tttatatttg ataaatatat tatttgcctt atctgacgta      60
aaaggtatat caacacatga tacatgcgat gaatggtcag aatggtctgc atgtactcat     120
ggaatcagta ccaggaaatg tttaagtgat tcttctatta aggatgagac acttgtatgt     180
acaaaatgtg ataaatgggg agaatggtca gaatgtaaag atgggagaat gcatagaaaa     240
gttttgaatt gtccttttat taagaagaa caagaatgtg atgtaaataa tgaaatggcg      300
gaggacacac atatgaataa tagctatata tatttcaacg cagatgatgg tgataatgaa     360
tatgaagatc atgatgataa aaatgatgat gataaaaatt atgataatga aaatgatgat     420
gataaatatg atgatgataa aaatgatgat gataaaaatg atgatgataa aaatgatgat     480
gaggaaaatt ataatgatac tgaagaaaag gtaaaaaata atgatataca taattctagt     540
gctaatagta ataatgaggt tactaatttc atacagataa aagataaaat tatgattaaa     600
cataaaacaa caaatataca tccagtgaat tttatacaag aaaaatatac aagaaatat       660 aaacatagat ctgataattt ttctaaaata ttaaataaca tgaatcatat aaataataat     720
aattataata gtagaagtag tagtacttct tcgaaaaatg ctagaggtta tagaggagga     780
agcagtaata tgtatccaca tgtaccaaat tacacgagtt cttctgtaca taatagtaca     840
aataatgaaa gaaaagtga tgaagacttg gataatatag agggtgataa taactaaaa       900 gaagaaagga ttgttccaat aaataacaaa aattatgata tcatgatga acatagtaat      960 atacacgagc atgatacatc tcgtaatgta gataatgaaa aatataattc aaatgatgat    1020
ttaccaaact tgtcgactta tgattatgat atgaataatg attcttataa aaagaatcac    1080
atgaaaaaac ctatggattc tattaaagaa gaacaaacaa aacaagaaaa taatcagaac    1140
aatgaaaaag tatcctcctc agaaaaacaa aatgatgata tatctgcatt atatgaacat    1200
atgaatacca aggatcaaga gcatacacaa catgaacaac caaatgacag tgcacatggt    1260
cactttgaag attacagtaa attatatatt gctagtggtg tagctactct tgtactcttg    1320
```

```
ggaggaagta taactttcta tttcttacgt aaagaaaaaa cagaaaaagt tgtacaagaa    1380
gaaacaaaag aggaaaactt tgaagtcatg tttaatgatg atgctctcaa gggaaaggat    1440
aacaaagcta tggatgaaga agaattctgg gcactcgaat ga                       1482
```

<210> SEQ ID NO 7
<211> LENGTH: 498
<212> TYPE: PRT
<213> ORGANISM: Plasmodium falciparum strain HB3

<400> SEQUENCE: 7

```
Met Lys Lys Thr Ile Leu Asn Leu Tyr Leu Ile Asn Ile Leu Phe Ala
 1               5                  10                  15

Leu Ser Asp Val Lys Gly Ile Ser Thr His Asp Thr Cys Asp Glu Trp
            20                  25                  30

Ser Glu Trp Ser Ala Cys Thr His Gly Ile Ser Thr Arg Lys Cys Leu
        35                  40                  45

Ser Asp Ser Ser Ile Lys Asp Glu Thr Leu Val Cys Thr Lys Cys Asp
    50                  55                  60

Lys Trp Gly Glu Trp Ser Glu Cys Lys Asp Gly Arg Met His Arg Lys
65                  70                  75                  80

Val Leu Asn Cys Pro Phe Ile Lys Glu Glu Gln Glu Cys Asp Val Asn
                85                  90                  95

Asn Glu Met Ala Glu Asp Thr His Met Asn Asn Ser Tyr Ile Tyr Phe
            100                 105                 110

Asn Ala Asp Asp Gly Asp Asn Glu Tyr Glu Asp His Asp Asp Lys Asn
        115                 120                 125

Asp Asp Asp Lys Asn Tyr Asp Asn Glu Asn Asp Asp Asp Lys Asn Asp
    130                 135                 140

Asp Asp Lys Asn Asp Asp Lys Asn Asp Asp Asp Lys Asn Asp Asp Asp
145                 150                 155                 160

Asp Lys Asn Asp Asp Glu Glu Asn Tyr Asn Asp Thr Glu Glu Lys Val
                165                 170                 175

Lys Asn Asn Asp Ile His Asn Ser Ser Ala Asn Ser Asn Asn Glu Val
            180                 185                 190

Thr Asn Phe Ile Gln Ile Lys Asp Lys Ile Met Ile Lys His Lys Thr
        195                 200                 205

Thr Asn Ile His Pro Val Asn Phe Ile Gln Glu Lys Tyr Thr Arg Asn
    210                 215                 220

Asn Lys Tyr Arg Ser Asp Asn Phe Ser Lys Ile Leu Asn Asn Met Asn
225                 230                 235                 240

His Ile Asn Asn Asn Asn Tyr Asn Ser Arg Ser Ser Thr Ser Ser
                245                 250                 255

Lys Asn Ala Arg Gly Tyr Arg Gly Gly Ser Ser Asn Met Tyr Pro His
            260                 265                 270

Val Pro Asn Tyr Thr Ser Ser Val His Ser Thr Asn Asn Glu
        275                 280                 285

Arg Lys Ser Asp Glu Asp Leu Asp Asn Ile Glu Gly Asp Asn Ile Thr
    290                 295                 300

Lys Glu Glu Arg Ile Val Pro Ile Asn Asn Lys Asn Tyr Asp Asn His
305                 310                 315                 320

Asp Glu His Ser Asn Ile His Glu His Asp Thr Ser Arg Asn Val Asp
                325                 330                 335

Asn Glu Lys Tyr Asn Ser Asn Asp Asp Leu Pro Asn Leu Ser Thr Tyr
```

```
               340                 345                 350
Asp Tyr Asp Met Asn Asn Asp Ser Tyr Lys Lys Asn His Met Lys Lys
                355                 360                 365

Pro Met Asp Ser Ile Lys Glu Glu Gln Thr Lys Gln Glu Asn Asn Gln
            370                 375                 380

Asn Asn Glu Lys Val Ser Ser Ser Glu Lys Gln Asn Asp Asp Ile Ser
385                 390                 395                 400

Ala Leu Tyr Glu His Met Asn Thr Lys Asp Gln Glu His Thr Gln His
                405                 410                 415

Glu Gln Pro Asn Asp Ser Ala His Gly His Phe Glu Asp Tyr Ser Lys
            420                 425                 430

Leu Tyr Ile Ala Ser Gly Val Ala Thr Leu Val Leu Leu Gly Gly Ser
                435                 440                 445

Ile Thr Phe Tyr Phe Leu Arg Lys Glu Lys Thr Glu Lys Val Val Gln
            450                 455                 460

Glu Glu Thr Lys Glu Glu Asn Phe Glu Val Met Phe Asn Asp Asp Ala
465                 470                 475                 480

Leu Lys Gly Lys Asp Asn Lys Ala Met Asp Glu Glu Glu Phe Trp Ala
                485                 490                 495

Leu Glu

<210> SEQ ID NO 8
<211> LENGTH: 1497
<212> TYPE: DNA
<213> ORGANISM: Plasmodium falciparum strain HB3

<400> SEQUENCE: 8
atgaagaaaa caatcctaaa tttatatttg ataaatatat tatttgcctt atctgacgta      60
aaaggtatat caacacatga tacatgcgat gaatggtcag aatggtctgc atgtactcat     120
ggaatcagta ccaggaaatg tttaagtgat tcttctatta aggatgagac acttgtatgt     180
acaaaatgtg ataaatgggg agaatggtca gaatgtaaag atgggagaat gcatagaaaa     240
gttttgaatt gtccttttat taaagaagaa caagaatgtg atgtaaataa tgaaatggcg     300
gaggacacac atatgaataa tagctatata tatttcaacg cagatgatgg tgataatgaa     360
tatgaagatc atgatgataa aaatgatgat gataaaaatt atgataatga aaatgatgat     420
gataaaaatg atgatgataa aaatgatgat gataaaaatg atgatgataa aaatgatgat     480
gataaaaatg atgatgagga aaattataat gatactgaag aaaaggtaaa aaataatgat     540
atacataatt ctagtgctaa tagtaataat gaggttacta atttcataca gataaaagat     600
aaaattatga ttaaacataa aacaacaaat atacatccag tgaattttat acaagaaaaa     660
tatacaagaa ataataaata tagatctgat aattttttcta aaatattaaa taacatgaat     720
catataaata ataataatta taatagtaga agtagtagta cttcttcgaa aaatgctaga     780
ggttatagag gaggaagcag taatatgtat ccacatgtac caattacac gagttcttct     840 gtacataata gtacaaataa tgaaagaaaa agtgatgaag acttggataa tatagagggt     900
gataatataa ctaagaaga aaggattgtt ccaataaata caaaaatta tgataatcat     960 gatgaacata gtaatataca cgagcatgat acatctcgta atgtagataa tgaaaaatat    1020
aattcaaatg atgatttacc aaacttgtcg acttatgatt atgatatgaa taatgattct    1080
tataaaaaga atcacatgaa aaacctatg gattctatta agaagaaca acaaaacaa     1140 gaaaataatc agaacaatga aaagtatcc tcctcagaaa acaaaatga tgatatatct    1200
```

-continued

```
gcattatatg aacatatgaa taccaaggat caagagcata cacaacatga acaaacaaat    1260
gacagtgcac atggtcactt tgaagattac agtaaattat atattgctag tggtgtagct    1320
actcttgtac tcttgggagg aagtataact ttctatttct tacgtaaaga aaaaacagaa    1380
aaagttgtac aagaagaaac aaaagaggaa aactttgaag tcatgtttaa tgatgatgct    1440
ctcaagggaa aggataacaa agctatggat gaagaagaat tctgggcact cgaatga       1497
```

<210> SEQ ID NO 9
<211> LENGTH: 498
<212> TYPE: PRT
<213> ORGANISM: Plasmodium falciparum strain M24

<400> SEQUENCE: 9

```
Met Lys Lys Thr Ile Leu Asn Leu Tyr Leu Ile Asn Ile Leu Phe Ala
1               5                   10                  15

Leu Ser Asp Val Lys Gly Ile Ser Thr His Asp Thr Cys Asp Glu Trp
            20                  25                  30

Ser Glu Trp Ser Ala Cys Thr His Gly Ile Ser Thr Arg Lys Cys Leu
        35                  40                  45

Ser Asp Ser Ser Ile Lys Asp Glu Thr Leu Val Cys Thr Lys Cys Asp
    50                  55                  60

Lys Trp Gly Glu Trp Ser Glu Cys Lys Asp Gly Arg Met His Arg Lys
65                  70                  75                  80

Val Leu Asn Cys Pro Phe Ile Lys Glu Glu Gln Glu Cys Asp Val Asn
                85                  90                  95

Asn Glu Met Ala Glu Asp Thr His Met Asn Asn Ser Tyr Ile Tyr Phe
            100                 105                 110

Asn Ala Asp Asp Gly Asp Asn Glu Tyr Glu Asp His Asp Asp Lys Asn
        115                 120                 125

Asp Asp Asp Lys Asn Tyr Asp Asn Glu Asn Asp Asp Lys Asn Asp
    130                 135                 140

Asp Asp Lys Asn Asp Asp Lys Asn Asp Asp Lys Asn Asp
145                 150                 155                 160

Asp Lys Asn Asp Asp Glu Glu Asn Tyr Asn Asp Thr Glu Glu Lys Val
                165                 170                 175

Lys Asn Asn Asp Ile His Asn Ser Ser Ala Asn Ser Asn Asn Glu Val
            180                 185                 190

Thr Asn Phe Ile Gln Ile Lys Asp Lys Ile Met Ile Lys His Lys Thr
        195                 200                 205

Thr Asn Ile His Pro Val Asn Phe Ile Gln Glu Lys Tyr Thr Arg Asn
    210                 215                 220

Asn Lys Tyr Arg Ser Asp Asn Phe Ser Lys Ile Leu Asn Asn Met Asn
225                 230                 235                 240

His Ile Asn Asn Asn Tyr Asn Ser Arg Ser Ser Ser Thr Ser Ser
                245                 250                 255

Lys Asn Ala Arg Gly Tyr Arg Gly Gly Ser Ser Asn Met Tyr Pro His
            260                 265                 270

Val Pro Asn Tyr Thr Ser Ser Val His Asn Ser Thr Asn Asn Glu
        275                 280                 285

Arg Lys Ser Asp Glu Asp Leu Asp Asn Ile Glu Gly Asp Asn Ile Thr
    290                 295                 300

Lys Glu Glu Arg Ile Val Pro Ile Asn Asn Lys Asn Tyr Asp Asn His
305                 310                 315                 320

Asp Glu His Ser Asn Ile His Glu His Asp Thr Ser Arg Asn Val Asp
```

|  |  | 325 |  |  |  | 330 |  |  |  | 335 |  |
|--|--|--|--|--|--|--|--|--|--|--|--|

Asn Glu Lys Tyr Asn Ser Asn Asp Asp Leu Pro Asn Leu Ser Thr Tyr
                        340                 345                 350

Asp Tyr Asp Met Asn Asn Asp Ser Tyr Lys Lys Asn His Met Lys Lys
            355                 360                 365

Pro Met Asp Ser Ile Lys Glu Glu Gln Thr Lys Gln Glu Asn Asn Gln
        370                 375                 380

Asn Asn Glu Lys Val Ser Ser Ser Glu Lys Gln Asn Asp Asp Ile Ser
385                 390                 395                 400

Ala Leu Tyr Glu His Met Asn Thr Lys Asp Gln Glu His Thr Gln His
                405                 410                 415

Glu Gln Pro Asn Asp Ser Ala His Gly His Phe Glu Asp Tyr Ser Lys
            420                 425                 430

Leu Tyr Ile Ala Ser Gly Val Ala Thr Leu Val Leu Leu Gly Gly Ser
        435                 440                 445

Ile Thr Phe Tyr Phe Leu Arg Lys Glu Lys Thr Glu Lys Val Val Gln
    450                 455                 460

Glu Glu Thr Lys Glu Glu Asn Phe Glu Val Met Phe Asn Asp Asp Ala
465                 470                 475                 480

Leu Lys Gly Lys Asp Asn Lys Ala Met Asp Glu Glu Phe Trp Ala
                485                 490                 495

Leu Glu

<210> SEQ ID NO 10
<211> LENGTH: 1497
<212> TYPE: DNA
<213> ORGANISM: Plasmodium falciparum strain M24

<400> SEQUENCE: 10

| | | |
|--|--|--|
| atgaagaaaa caatactaaa tttatatttg ataaatatat tatttgcctt atctgacgta | 60 |
| aaaggtatat caacacatga tacatgcgat gaatggtcag aatggtctgc atgtactcat | 120 |
| ggaatcagta ccaggaaatg tttaagtgat tcttctatta aggatgagac acttgtatgt | 180 |
| acaaaatgtg ataaatgggg agaatggtca gaatgtaaag atgggagaat gcatagaaaa | 240 |
| gttttgaatt gtccttttat taagaagaa caagaatgtg atgtaaataa tgaaatggcg | 300 |
| gaggacacac atatgaataa tagctatata tatttcaacg cagatgatgg tgataatgaa | 360 |
| tatgaagatc atgatgataa aaatgatgat gataaaaatt atgataatga aaatgatgat | 420 |
| gataaaaatg atgatgataa aaatgatgat gataaaaatg atgatgataa aaatgatgat | 480 |
| gataaaaatg atgatgagga aaattataat gatactgaag aaaaggtaaa aataatgat | 540 |
| atacataatt ctagtgctaa tagtaataat gaggttacta atttcataca gataaaagat | 600 |
| aaaattatga ttaaacataa acaacaaat atacatccag tgaatttat acaagaaaaa | 660 |
| tatacaagaa ataataaata tagatctgat aattttttcta aaatattaaa taacatgaat | 720 |
| catataaata taataatta atagtagaa agtagtagta cttcttcgaa aaatgctaga | 780 |
| ggttatagag gaggaagcag taatatgtat ccacatgtac caattacac gagttcttct | 840 |
| gtacataata gtacaaataa tgaaagaaaa agtgatgaag acttggataa tatagagggt | 900 |
| gataatataa ctaagaaga aaggattgtt ccaataaata acaaaaatta tgataatcat | 960 |
| gatgaacata gtaatataca cgagcatgat acatctcgta atgtagataa tgaaaaatat | 1020 |
| aattcaaatg atgatttacc aaacttgtcg acttatgatt atgatatgaa taatgattct | 1080 |
| tataaaaaga atcacatgaa aaaacctatg gattctatta agaagaaca aacaaaacaa | 1140 |

```
gaaaataatc agaacaatga aaaagtatcc tcctcagaaa aacaaaatga tgatatatct    1200
gcattatatg aacatatgaa taccaaggat caagagcata cacaacatga acaaccaaat    1260
gacagtgcac atggtcactt tgaagattac agtaaattat atattgctag tggtgtagct    1320
actcttgtac tcttgggagg aagtataact ttctatttct tacgtaaaga aaaaacagaa    1380
aaagttgtac aagaagaaac aaaagaggaa aactttgaag tcatgtttaa tgatgatgct    1440
ctcaagggaa aggataacaa agctatggat gaagaagaat tctgggcact cgaatga       1497

<210> SEQ ID NO 11
<211> LENGTH: 503
<212> TYPE: PRT
<213> ORGANISM: Plasmodium falciparum strain MCAMP

<400> SEQUENCE: 11

Met Lys Lys Thr Ile Leu Asn Leu Tyr Leu Ile Asn Ile Leu Phe Ala
1               5                   10                  15

Leu Ser Asp Val Lys Gly Ile Ser Thr His Asp Thr Cys Asp Glu Trp
            20                  25                  30

Ser Glu Trp Ser Ala Cys Thr His Gly Ile Ser Thr Arg Lys Cys Leu
        35                  40                  45

Ser Asp Ser Ser Ile Lys Asp Glu Thr Leu Val Cys Thr Lys Cys Asp
    50                  55                  60

Lys Trp Gly Glu Trp Ser Glu Cys Lys Asp Gly Arg Met His Arg Lys
65                  70                  75                  80

Val Leu Asn Cys Pro Phe Ile Lys Glu Glu Gln Glu Cys Asp Val Asn
                85                  90                  95

Asn Glu Met Ala Glu Asp Thr His Met Asn Asn Ser Tyr Ile Tyr Phe
            100                 105                 110

Asn Ala Asp Asp Gly Asp Asn Glu Tyr Glu Asp His Asp Asp Lys Asn
        115                 120                 125

Asp Asp Asp Lys Asn Tyr Asp Asn Glu Asn Asp Asp Lys Asn Asp
    130                 135                 140

Asp Asp Lys Asn Asp Asp Lys Asn Asp Asp Lys Asn Asp
145                 150                 155                 160

Asp Lys Asn Asp Asp Lys Asn Asp Asp Glu Glu Asn Tyr Asn Asp
                165                 170                 175

Thr Glu Glu Lys Val Lys Asn Asn Asp Ile His Asn Ser Ser Ala Asn
            180                 185                 190

Ser Asn Asn Glu Val Thr Asn Phe Ile Gln Ile Lys Asp Lys Ile Met
        195                 200                 205

Ile Lys His Lys Thr Thr Asn Ile His Pro Val Asn Phe Ile Gln Glu
    210                 215                 220

Lys Tyr Thr Arg Asn Asn Lys Tyr Arg Ser Asp Asn Phe Ser Lys Ile
225                 230                 235                 240

Leu Asn Asn Met Asn His Ile Asn Asn Asn Tyr Asn Ser Arg Ser
                245                 250                 255

Ser Ser Thr Ser Ser Lys Asn Ala Arg Gly Tyr Arg Gly Ser Ser
            260                 265                 270

Asn Met Tyr Pro His Val Pro Asn Tyr Thr Ser Ser Val His Asn
        275                 280                 285

Ser Thr Asn Asn Glu Arg Lys Ser Asp Glu Asp Leu Asp Asn Ile Glu
    290                 295                 300

Gly Asp Asn Ile Thr Lys Glu Glu Arg Ile Val Pro Ile Asn Asn Lys
```

|   |   |   | 305 |   |   |   | 310 |   |   |   | 315 |   |   |   | 320 |
|---|---|---|-----|---|---|---|-----|---|---|---|-----|---|---|---|-----|

Asn Tyr Asp Asn His Asp Glu His Ser Asn Ile His Glu His Asp Thr
                325                 330                 335

Ser Arg Asn Val Asp Asn Glu Lys Tyr Asn Ser Asn Asp Asp Leu Pro
                340                 345                 350

Asn Leu Ser Thr Tyr Asp Tyr Asp Met Asn Asn Asp Ser Tyr Lys Lys
                355                 360                 365

Asn His Met Lys Lys Pro Met Asp Ser Ile Lys Glu Glu Gln Thr Lys
                370                 375                 380

Gln Glu Asn Asn Gln Asn Asn Glu Lys Val Ser Ser Ser Glu Lys Gln
385                 390                 395                 400

Asn Asp Asp Ile Ser Ala Leu Tyr Glu His Met Asn Thr Lys Asp Gln
                405                 410                 415

Glu His Thr Gln His Glu Gln Thr Asn Asp Ser Ala His Gly His Phe
                420                 425                 430

Glu Asp Tyr Ser Lys Leu Tyr Ile Ala Ser Gly Val Ala Thr Leu Val
                435                 440                 445

Leu Leu Gly Gly Ser Ile Thr Phe Tyr Phe Leu Arg Lys Glu Lys Thr
450                 455                 460

Glu Lys Val Val Gln Glu Gly Thr Lys Glu Glu Asn Phe Glu Val Met
465                 470                 475                 480

Phe Asn Asp Asp Ala Leu Lys Gly Lys Asp Asn Lys Ala Met Asp Glu
                485                 490                 495

Glu Glu Phe Trp Ala Leu Glu
                500

<210> SEQ ID NO 12
<211> LENGTH: 1512
<212> TYPE: DNA
<213> ORGANISM: Plasmodium falciparum strain MCAMP

<400> SEQUENCE: 12

```
atgaagaaaa caatactaaa tttatatttg ataaatatat tatttgcctt atctgacgta      60
aaaggtatat caacacatga tacatgcgat gaatggtcag aatggtctgc atgtactcat     120
ggaatcagta ccaggaaatg tttaagtgat tcttctatta aggatgagac acttgtatgt     180
acaaaatgtg ataaatgggg agaatggtca gaatgtaaag atgggagaat gcatagaaaa     240
gttttgaatt gtccttttat taagaagaa caagaatgtg atgtaaataa tgaaatggcg      300
gaggacacac atatgaataa tagctatata tatttcaacg cagatgatgg tgataatgaa     360
tatgaagatc atgatgataa aaatgatgat gataaaaatt atgataatga aaatgatgat     420
gataaaaatg atgatgataa aaatgatgat gataaaaatg atgatgataa aaatgatgat     480
gataaaaatg atgatgataa aaatgatgat gaggaaaatt ataatgatac tgaagaaaag     540
gtaaaaaata tgatataca taattctagt gctaatagta ataatgaggt tactaatttc     600
atacagataa aagataaaat tatgattaaa cataaaacaa caatatacaa tccagtgaat      660
tttatacaag aaaaatatac aagaaataat aaatatagat ctgataattt ttctaaaata     720
ttaaataaca tgaatcatat aaataataat aattataata gtagaagtag tagtacttct     780
tcgaaaaatg ctagaggtta tagaggagga agcagtaata tgtatccaca tgtaccaaat     840
tacacgagtt cttctgtaca taatagtaca ataatgaaa gaaaagtga tgaagacttg      900
gataatatag agggtgataa tataactaaa gaagaaagga ttgttccaat aaataacaaa     960
aattatgata atcatgatga acatagtaat atacacgagc atgatacatc tcgtaatgta    1020
```

```
gataatgaaa aatataattc aaatgatgat ttaccaaact tgtcgactta tgattatgat    1080
atgaataatg attcttataa aaagaatcac atgaaaaaac ctatggattc tattaaagaa    1140
gaacaaacaa aacaagaaaa taatcagaac aatgaaaaag tatcctcctc agaaaaacaa    1200
aatgatgata tatctgcatt atatgaacat atgaatacca aggatcaaga gcatacacaa    1260
catgaacaac caaatgacag tgcacatggt cactttgaag attacagtaa attatatatt    1320
gctagtggtg tagctactct tgtactcttg ggaggaagta taactttcta tttcttacgt    1380
aaagaaaaaa cagaaaaagt tgtacaagaa gaaacaaaag aggaaaactt tgaagtcatg    1440
tttaatgatg atgctctcaa gggaaaggat aacaaagcta tggatgaaga agaattctgg    1500
gcactcgaat ga                                                        1512

<210> SEQ ID NO 13
<211> LENGTH: 488
<212> TYPE: PRT
<213> ORGANISM: Plasmodium falciparum strain C2A

<400> SEQUENCE: 13

Met Lys Lys Thr Ile Leu Asn Leu Tyr Leu Ile Asn Ile Leu Phe Ala
1               5                   10                  15

Leu Ser Asp Val Lys Gly Ile Ser Thr His Asp Thr Cys Asp Glu Trp
            20                  25                  30

Ser Glu Trp Ser Ala Cys Thr His Gly Ile Ser Thr Arg Lys Cys Leu
        35                  40                  45

Ser Asp Ser Ser Ile Lys Asp Glu Thr Leu Val Cys Thr Lys Cys Asp
    50                  55                  60

Lys Trp Gly Glu Trp Ser Glu Cys Lys Asp Gly Arg Met His Arg Lys
65                  70                  75                  80

Val Leu Asn Cys Pro Phe Ile Lys Glu Glu Gln Glu Cys Asp Val Asn
                85                  90                  95

Asn Glu Met Ala Glu Asp Thr His Met Asn Asn Ser Tyr Ile Tyr Phe
            100                 105                 110

Asn Ala Asp Asp Gly Asp Asn Glu Tyr Glu Asp His Asp Asp Lys Asn
        115                 120                 125

Asp Asp Asp Lys Asn Tyr Asp Asn Glu Asn Asp Asp Lys Asn Asp
    130                 135                 140

Asp Asp Lys Asn Asp Asp Lys Asn Asp Asp Glu Glu Asn Tyr Asn
145                 150                 155                 160

Asp Thr Glu Glu Lys Val Lys Asn Asn Asp Ile His Asn Ser Ser Ala
                165                 170                 175

Asn Ser Asn Asn Glu Val Thr Asn Phe Ile Gln Ile Lys Asp Lys Ile
            180                 185                 190

Met Ile Lys His Lys Thr Thr Asn Ile His Pro Val Asn Phe Ile Gln
        195                 200                 205

Glu Lys Tyr Thr Arg Asn Asn Lys His Arg Ser Asp Asn Phe Ser Lys
    210                 215                 220

Ile Leu Asn Asn Met Asn His Ile Asn Asn Asn Tyr Asn Ser Arg
225                 230                 235                 240

Ser Ser Ser Thr Ser Ser Lys Asn Ala Arg Gly Tyr Arg Gly Gly Ser
                245                 250                 255

Ser Asn Met Tyr Pro His Val Pro Asn Tyr Thr Ser Ser Ser Val His
            260                 265                 270

Asn Ser Thr Asn Asn Glu Arg Lys Ser Asp Glu Asp Leu Asp Asn Ile
```

```
              275                 280                 285
Glu Gly Asp Asn Ile Thr Lys Glu Glu Arg Ile Val Pro Ile Asn Asn
            290                 295                 300

Lys Asn Tyr Asp Asn His Asp Glu His Ser Asn Ile His Glu His Asp
305                 310                 315                 320

Thr Ser Arg Asn Val Asp Asn Glu Lys Tyr Asn Ser Asn Asp Asp Leu
                325                 330                 335

Pro Asn Leu Ser Thr Tyr Asp Tyr Asp Met Asn Asn Asp Ser Tyr Lys
            340                 345                 350

Lys Asn His Met Lys Lys Pro Met Asp Ser Ile Lys Glu Glu Gln Thr
        355                 360                 365

Lys Gln Glu Asn Asn Gln Asn Asn Glu Lys Val Ser Ser Ser Glu Lys
    370                 375                 380

Gln Asn Asp Asp Ile Ser Ala Leu Tyr Glu His Met Asn Thr Lys Asp
385                 390                 395                 400

Gln Glu His Thr Gln His Glu Gln Pro Asn Asp Ser Ala His Gly His
                405                 410                 415

Phe Glu Asp Tyr Ser Lys Leu Tyr Ile Ala Ser Gly Val Ala Thr Leu
            420                 425                 430

Val Leu Leu Gly Gly Ser Ile Thr Phe Tyr Phe Leu Arg Lys Glu Lys
        435                 440                 445

Thr Glu Lys Val Val Gln Glu Glu Thr Lys Glu Glu Asn Phe Glu Val
    450                 455                 460

Met Phe Asn Asp Asp Ala Leu Lys Gly Lys Asp Asn Lys Ala Met Asp
465                 470                 475                 480

Glu Glu Glu Phe Trp Ala Leu Glu
                485

<210> SEQ ID NO 14
<211> LENGTH: 1467
<212> TYPE: DNA
<213> ORGANISM: Plasmodium falciparum strain C2A

<400> SEQUENCE: 14
atgaagaaaa caatactaaa tttatatttg ataaatatat tatttgcctt atctgacgta     60
aaaggtatat caacacatga tacatgcgat gaatggtcag aatggtctgc atgtactcat    120
ggaatcagta ccaggaaatg tttaagtgat tcttctatta aggatgagac acttgtatgt    180
acaaaatgtg ataaatgggg agaatggtca gaatgtaaag atgggagaat gcatagaaaa    240
gttttgaatt gtccttttat taagaagaa caagaatgtg atgtaaataa tgaaatggcg    300
gaggacacac atatgaataa tagctatata tatttcaacg cagatgatgg tgataatgaa    360
tatgaagatc atgatgataa aaatgatgat gataaaaatt atgataatga aaatgatgat    420
gataaaaatg atgatgataa aaatgatgat gataaaaatg atgatgagga aaattataat    480
gatactgaag aaaaggtaaa aaataatgat atacataatt ctagtgctaa tagtaataat    540
gaggttacta atttcataca gataaaagat aaaattatga ttaaacataa acaacaaat    600 atacatccag tgaatttttat acaagaaaaa tatacaagaa ataataaaca tagatctgat    660
aattttctaa aaatattaaa taacatgaat catataaata ataataatta aatagtaga    720 agtagtagta cttcttcgaa aaatgctaga ggttatagag aggaagcag taatatgtat    780 ccacatgtac caaattacac gagttcttct gtacataata gtacaaataa tgaaagaaaa    840
agtgatgaag acttggataa atagagggt gataatataa ctaaagaaga aaggattgtt    900
```

-continued

```
ccaataaata acaaaaatta tgataatcat gatgaacata gtaatataca cgagcatgat    960
acatctcgta atgtagataa tgaaaaatat aattcaaatg atgatttacc aaacttgtcg   1020
acttatgatt atgatatgaa taatgattct tataaaaaga atcacatgaa aaacctatg    1080
gattctatta agaagaaca acaaaaacaa gaaataatc agaacaatga aaagtatcc     1140
tcctcagaaa acaaaatga tgatatatct gcattatatg aacatatgaa taccaaggat   1200
caagagcata cacaacatga acaaacaaat gacagtgcac atggtcactt tgaagattac   1260
agtaaattat atattgctag tggtgtagct actcttgtac tcttgggagg aagtataact   1320
ttctatttct tacgtaaaga aaaaacagaa aaagttgtac aagaagaaac aaaagaggaa   1380
aactttgaag tcatgtttaa tgatgatgct ctcaagggaa aggataacaa agctatggat   1440
gaagaagaat tctgggcact cgaatga                                       1467
```

<210> SEQ ID NO 15
<211> LENGTH: 387
<212> TYPE: PRT
<213> ORGANISM: Plasmodium vivax

<400> SEQUENCE: 15

```
Met Lys Met Ala Ser Phe Lys Ser Leu Leu Leu Asn Ile Phe Phe Phe
1               5                   10                  15

Ser Leu Ile Gln Ile Ser Cys Lys Arg Ile Gly Lys Arg Lys Cys Glu
            20                  25                  30

Gln Trp Asp Ser Trp Ser Ala Cys Lys Asp Gly Ile Ser Thr Arg Val
        35                  40                  45

Cys Leu Thr Asn Lys Ser Val Thr Asp Lys Met Thr Cys Lys Ala Cys
    50                  55                  60

Asn Ile Trp Gly Asp Trp Ser Ala Cys Lys Asn Gly Lys Arg His Arg
65                  70                  75                  80

Lys Val Val Asn Cys Pro Phe Ile Arg Glu Glu Gln Asp Cys Asp Pro
                85                  90                  95

Asn Lys Ser Asn Lys Gln Asn Ala Arg Asn Asn Thr Thr Ile Tyr Phe
            100                 105                 110

Asn Asn Asp Asp Tyr Asp Asp Glu Gln Asp Asp Val Phe Glu Glu Thr
        115                 120                 125

Leu Gln Glu Glu Ser Asn Leu Pro Val Lys Gly Asp Ser Ser Glu Pro
    130                 135                 140

Ile Phe Leu Glu Gln Asp Ser His Gly Glu Gly Lys Gln Gln Ser Met
145                 150                 155                 160

Ser Glu Ser Phe Ala His Val Asp Glu Val Asp Ala Thr Ala Gln Pro
                165                 170                 175

His Asn Glu Val Leu Thr Asp Thr Thr Thr Pro Ser Gly Ala Ser Pro
            180                 185                 190

Pro Ala Asp Asp Ala Asn Asn Glu Thr Tyr Val Ser Tyr Pro Glu Glu
        195                 200                 205

Glu Pro Leu His Gly Pro Gln Asn Asn Ser Asp Glu Ala Gln Ala Gly
    210                 215                 220

Ala Asp His Leu Ser Ser His Asn Leu Ala Asp Gln Ala Asp Ser
225                 230                 235                 240

Gln Ala Asp Gly Gln Thr Asn Ala Ala Pro Ser Ser Glu Pro Arg Ala
                245                 250                 255

Lys His Phe Arg Asp His Lys Phe Glu Asp Val Ser Ser Pro Pro Gly
            260                 265                 270
```

-continued

```
Glu Gly Gln Asn Glu Asn His Ala Glu Gly Asn Thr Asn Gln Asn Ser
            275                 280                 285

Phe Tyr Glu Gln Gln Gly Ser His His Glu His Ser Glu His Lys Trp
290                 295                 300

Arg Lys Lys His Asn Ala Gly Ala Gly Ser Gly Gly Ala Pro Lys Phe
305                 310                 315                 320

Asn Gln Thr Tyr Ile Ala Ser Gly Met Gly Leu Leu Phe Leu Leu Ser
                325                 330                 335

Gly Thr Ala Ala Ser Tyr Ala Leu Tyr Asn Gly Lys Tyr Lys Glu Leu
            340                 345                 350

Thr Glu Glu Ala Lys Asn Glu Asn Phe Glu Val Ile Phe Asn Glu Asp
            355                 360                 365

Met Lys Ala Arg Glu Asn Ser Lys Ser Met Tyr Glu Asp Glu Phe Trp
370                 375                 380

Ala Leu Gly
385

<210> SEQ ID NO 16
<211> LENGTH: 375
<212> TYPE: PRT
<213> ORGANISM: Plasmodium knowlesi

<400> SEQUENCE: 16

Met Ala Ser Phe Lys Ser Leu Leu Leu Asn Ile Phe Phe Phe Ser Leu
1               5                   10                  15

Ile His Ile Ser Cys Glu Leu Ile Arg Asp Lys Arg Cys Glu Gln Trp
            20                  25                  30

Asp Ser Trp Ser Pro Cys Lys Asn Gly Ile Ser Thr Arg Ile Cys Leu
        35                  40                  45

Thr Asp Lys Ser Val Thr Asp Lys Met Thr Cys Thr Met Cys Asn Ile
    50                  55                  60

Trp Gly Glu Trp Ser Ala Cys Gln Asn Gly Lys Arg His Arg Lys Ile
65                  70                  75                  80

Val Asn Cys Pro Phe Ile Arg Glu Asp Gln Asp Cys Asp Pro Asn Asn
                85                  90                  95

Ser Asn Glu Glu Asn Ala Arg Asn Asn Thr Ile Tyr Phe Asn Asn
            100                 105                 110

Tyr Asp Asp Glu Gln Gly Asp Asn Phe Glu Glu Thr Leu Glu Glu Glu
        115                 120                 125

Ser Asn Leu Pro Val Thr Gly Asp Asn Ser Glu Pro Val Phe Leu Glu
    130                 135                 140

Arg Asn Ser His Gly Glu Arg Lys Gln Gln Gly Met Arg Glu Ser Phe
145                 150                 155                 160

Ala His Val Asp Glu Val Asp Thr Thr Ala Gln Glu His Asn Asp Met
                165                 170                 175

Leu Thr Asp Thr Thr Pro Ser Glu Ala Ser Pro Pro Ala Asp Asp Ala
            180                 185                 190

Ser Glu Asn His Ala Lys Ser Pro Asn Pro Asp Glu Leu Asn Glu Pro
        195                 200                 205

His Ile Asn Ser Asp Gly Ala Gln Thr Asp Ala Thr Tyr Asp Pro Ser
    210                 215                 220

Ser His Asn Pro Ala Asp Gln Ser Asp Thr Ala Pro Phe Ser Lys
225                 230                 235                 240

Pro Lys Arg Ala Lys Asn Phe Arg Asp His Lys Phe Asp Phe Ser
                245                 250                 255
```

```
Ser Thr Pro Gly Glu Gly Gln Asn Lys Asn His Ala Glu Gly Asp Thr
            260             265             270

His Arg Gln Ser Phe Lys Glu Gln Gln Gly Asn Gln His Glu Gln Ser
        275             280             285

Lys Asn Glu Trp Arg Lys Lys His Asn Ala Gly Thr Gly Ser Gly Gly
        290             295             300

Ala Pro Lys Phe Asn Gln Thr Tyr Ile Ala Ser Gly Met Gly Leu Leu
305             310             315             320

Phe Leu Val Ser Gly Ser Ala Ala Ser Tyr Ala Leu Tyr Asn Gly Lys
            325             330             335

Tyr Lys Gln Leu Asn Glu Glu Ala Lys Asn Glu Asn Phe Glu Val Ile
            340             345             350

Phe Asn Glu Asp Met Lys Ala Arg Asp Asn Ser Lys Ser Met Tyr Glu
        355             360             365

Asp Glu Phe Trp Ala Leu Gly
    370             375
```